US007247484B2

(12) United States Patent
Wu et al.

(10) Patent No.: US 7,247,484 B2
(45) Date of Patent: Jul. 24, 2007

(54) HEMATOLOGY REAGENT AND METHODS

(75) Inventors: Jiong Wu, La Vista, NE (US); Wayne L. Ryan, Omaha, NE (US)

(73) Assignee: Streck, Inc., La Vista, NE (US)

( * ) Notice: Subject to any disclaimer, the term of this patent is extended or adjusted under 35 U.S.C. 154(b) by 436 days.

(21) Appl. No.: 10/699,502

(22) Filed: Oct. 31, 2003

(65) Prior Publication Data

US 2004/0142318 A1 Jul. 22, 2004

Related U.S. Application Data

(60) Provisional application No. 60/423,060, filed on Nov. 1, 2002.

(51) Int. Cl.
- G01N 31/00 (2006.01)
- G01N 33/48 (2006.01)
- A01N 1/02 (2006.01)
- C12Q 1/00 (2006.01)

(52) U.S. Cl. .......................... 436/17; 435/40.5; 435/2; 435/4

(58) Field of Classification Search .................. 435/2, 435/4, 372, 40.5; 436/17, 71
See application file for complete search history.

(56) References Cited

U.S. PATENT DOCUMENTS

| | | | | |
|---|---|---|---|---|
| 3,616,254 | A | | 10/1971 | Beutler .................. 435/15 |
| 4,217,345 | A | * | 8/1980 | Shinohara et al. .......... 514/33 |
| 4,250,051 | A | | 2/1981 | Armstrong ................ 252/408 |
| 4,529,705 | A | | 7/1985 | Larsen .................... 437/17 |
| 4,745,071 | A | | 5/1988 | Lapicola et al. ............ 436/63 |
| 5,155,044 | A | | 10/1992 | Ledis et al. ............... 436/17 |
| 5,188,935 | A | | 2/1993 | Leif et al. ............... 435/7.24 |
| 5,250,438 | A | | 10/1993 | Ryan ...................... 436/17 |
| 5,262,329 | A | | 11/1993 | Carver, Jr. ............... 436/63 |
| 5,320,964 | A | | 6/1994 | Young et al. .............. 436/10 |
| 5,348,859 | A | | 9/1994 | Brunhouse et al. ........ 435/7.24 |
| 5,486,477 | A | | 1/1996 | Carver, Jr. et al. .......... 436/17 |
| 5,512,485 | A | | 4/1996 | Young et al. .............. 436/10 |
| 5,516,695 | A | | 5/1996 | Kim et al. ................ 436/17 |
| 5,639,630 | A | * | 6/1997 | Malin et al. .............. 435/28 |
| 5,686,308 | A | | 11/1997 | Li et al. .................. 436/63 |
| 5,731,206 | A | | 3/1998 | Ledis et al. ............... 436/17 |
| 5,776,709 | A | | 7/1998 | Jackson et al. ............ 435/7.24 |
| 5,786,224 | A | | 7/1998 | Li et al. .................. 436/63 |
| 5,817,518 | A | | 10/1998 | Li et al. .................. 436/63 |
| 5,843,608 | A | | 12/1998 | Li et al. .................. 436/63 |
| 5,858,790 | A | | 1/1999 | Kim et al. ................ 436/16 |
| 5,928,949 | A | | 7/1999 | Sakata et al. ............. 436/17 |
| 6,187,590 | B1 | | 2/2001 | Kim et al. ................ 436/10 |
| 6,210,969 | B1 | | 4/2001 | Li et al. .................. 436/10 |
| 6,214,625 | B1 | | 4/2001 | Li et al. .................. 436/10 |
| 6,251,615 | B1 | | 6/2001 | Oberhardt ................ 435/7.21 |
| 6,509,192 | B1 | | 1/2003 | Young .................... 436/10 |
| 6,514,763 | B2 | | 2/2003 | Carver et al. ............. 436/10 |
| 6,653,137 | B2 | | 11/2003 | Ryan .................... 436/10 |
| 2002/0098589 | A1 | | 7/2002 | Crews et al. ............. 436/10 |

FOREIGN PATENT DOCUMENTS

| EP | 0 325 710 | 8/1989 |
|---|---|---|
| WO | WO 88 07187 | 9/1988 |

OTHER PUBLICATIONS

Segal et al. "Hemolytic properties of synthetic glycosides" J. Pharma. Sci. (1978) 67(11): 1589-1592.*
Dave, Raju S.; Loos, Alfred C., Eds. Processing of Composites. (2000)( Hanser Publishers: Munich), p. 203. Online version available at:http://www.knovel.com/knovel2/Toc.jsp?BookID=997&VerticalID=0; downloaded from the Web on Dec. 30, 2006.*
Bomford, R., "Studies on the Cellular Site of Action of the Adjuvant Activity of Saponin for Sheep Erythrocytes", *Int. Archs. Allergy and Immunology*, vol. 67, No. 2 (Feb. 1982); pp. 127-131.
Glauert, A.M.; Dingle, J.T.; Lucy, J.A., "Action of Saponin on Biological Cell Membranes", *Nature*, vol. 196, No. 4858 (Dec. 8, 1962); pp. 952-955.
Hase, J.; Kobashi, K.; Mitsui, K.; Namba, T.; Yoshizaki, M.; Tomimori, T., "The Structure-Hemolysis Relationship of Oleanolic Acid Derivatives and Inhibition of the Saponin-Induced Hemolysis with Sapogenins", *Journal of Pharmacobio-Dynamics*, vol. 4 (1981); pp. 833-837.
Owellen, R.J.; Owellen, R.G.; Gorog, M.A.; Klein, D., "Cytolytic Saponin Fraction From *Asterias Vulgaris*", *Toxicon*, vol. 11, No. 4 (Jul. 1973); pp. 319-323.
Segal, R.; Shatkovsky, P.; Milo-Goldzweig, I., "On the Mechanism of Saponin Hemolysis—I. Hydrolysis of the Glycosidic Bond", *Biochemical Pharmacology*, vol. 23, No. 5 (Mar. 1, 1974); pp. 973-981.
Segal R.; Milo-Goldzweig, I., "On the Mechanism of Saponin Hemolysis—II. Inhibition of Hemolysis by Aldonolactones", *Biochemical Pharmacology*, vol. 24, No. 1, (Jan. 1, 1975): pp. 77-81.
Segelman, A.B.; Farnsworth, N.R.; Quimby, M.W., "Biological and Phytochemical Evaluation of Plants. III. False-Negative Saponin Test Results Induced by the Presence of Tannis", *Lloydia*, vol. 32, No. 1 (Mar. 1969); pp. 52-58.
Tatsumi, N., "Alterations of Saponin Hemolysis During Storage of ACD Blood", *Vax Sanguinis*, vol. 41, No. 1 (Jul. 1981); pp. 18-24.

(Continued)

*Primary Examiner*—Leon B. Lankford, Jr.
*Assistant Examiner*—Susan Hanley
(74) *Attorney, Agent, or Firm*—Howrey LLP

(57) ABSTRACT

A reagent system is provided for substantially lysing red blood cells in a whole blood sample prior to leukocyte analysis, which system includes a first reagent for substantially lysing the red blood cells in the whole blood sample, and a second reagent for quenching the activity of the first reagent. The first reagent is formulated to include an autoclaved saponin compound and an acid selected from the group consisting of a halogenated carboxylic acid, a phosphoric acid and a combination thereof. The second reagent includes a base and has a pH value of about 8 to 12. Also provided is a method of lysing the red blood cells and stabilizing white blood cells present in a sample of whole blood.

7 Claims, 1 Drawing Sheet

OTHER PUBLICATIONS

Tatsumi, N.; Maeda, H.; Wada, Y., "The Contribution of Saponin Hemolysis in Observing Membrane Properties of Erythrocytes", *Acta Haematologica Japoncia*, vol. 45, No. 1, (Feb. 1982); pp. 31-37.

Ueda, S.; Harano, K.; Takemoto, Y.; Harano, T.; Shibata, S., "Continuous Measurement of the Change in Erythrocyte Volume After Addition of Saponin (Saponin Test)", Kawasaki Medical Journal, vol. 7, No. 2 (1981); pp. 127-135.

* cited by examiner

HEMATOLOGY REAGENT AND METHODS

This is a non-provisional of U.S. provisional application No. 60/423,060, filed Nov. 1, 2002 the contents of which are incorporated herein by reference.

BACKGROUND

Analysis of leukocyte populations from whole blood samples is an important diagnostic procedure. The ability to analyze the major subpopulations of leukocytes in an automated manner has proved to be an effective tool for a rapid diagnosis of one or more blood samples.

For a number of automated hematology analyzers, a blood sample is typically split into a first portion that is subjected to techniques for analysis of red blood cells. A second portion is also obtained from the sample, which is employed for white blood cell analysis. It is important during analysis of the second portion that red blood cells be substantially completely lysed so that they do not interfere with white blood cell analysis. Thus far, several lysis reagents have been developed for use in whole blood samples. The claimed subject matter constitutes an improvement relative to existing reagents.

SUMMARY

The subject matter of the present disclosure is generally directed to a reagent system for substantially lysing red blood cells in a whole blood sample prior to leukocyte analysis. In one illustrative embodiment, the reagent system includes a first reagent for substantially lysing the red blood cells in the whole blood sample, and a second reagent for quenching the activity of the first reagent, wherein the second reagent includes a base and has a pH value of about 8 to 12. A final acidic medium, ranging from about pH 3 to about 6, preferably from about 4 to about 5, is used to stabilize the white blood cells and continuously remove red blood cell fragments. The first reagent is formulated to include: a saponin compound; an acid, preferably selected from halogenated carboxylic acids, phosphoric acid or combinations of these and similar compounds that should be known to one of skill in the art. Optionally the first reagent may further include a surfactant preferably selected from non-ionic surfactants, cationic surfactants and combinations of these and similar compounds that should be known to one of skill in the art. In one specific and illustrative embodiment, the surfactant is selected from ethoxylated decylalcohols, ethoxylated and propoxylated linear (C8-C10) aliphatic alcohols, and combinations of these and similar compounds that should be known to one of skill in the art. It should be appreciated that the saponin compound is preferably selected from the group including saponin; heat-treated saponin, saponin modified by heating in the presence of a halogenated carboxylic acid and combinations of these and similar compounds that should be known to one of skill in the art.

Another illustrative embodiment of the claimed subject matter includes a reagent system formulated to include: a reagent for lysing red blood cells; and a quench; such that the system is substantially free of compounds including: i. dye; ii. a combination of saponin and carboxylic acid; iii. an acid selected from formic acid, acetic acid and mixtures thereof; iv. a combination of saponin and sulphonic acid; v. a cross-linking agent such as an aldehyde; vi. an alkali metal salt of an alkyl sulfate anionic surfactant; vii. an ethoxylated long chain amine; and viii. combinations thereof. A final acidic medium, ranging from about pH 3 to about 6, preferably from about 4 to about 5, is used to stabilize the white blood cells and continuously remove red blood cell fragments. Preferably the illustrative reagent for lysing red blood cells includes a saponin compound and an acid. The saponin compound can be selected from saponin; heat-treated saponin, saponin modified by heating in the presence of a halogenated carboxylic acid and combinations of these and similar compounds that should be known to one of skill in the art. The acid portion of the reagent system is selected from halogenated carboxylic acids, phosphoric acid or combinations of these and similar compounds that should be known to one of skill in the art. The reagent for lysing red blood cells may further include a surfactant. The surfactant can be selected from non-ionic surfactants, cationic surfactants and combinations thereof and preferably the surfactant is selected from ethoxylated decylalcohols, ethoxylated and propoxylated linear (C8-C10) aliphatic alcohols, and combinations of these and similar such compounds.

It will also be appreciated by one or ordinary skill in the art that an illustrative embodiment of the claimed subject matter includes a method of lysing the red blood cells present in a sample of whole blood. In one such illustrative embodiment, the method includes: combining a predetermined portion of the sample of whole blood with a predetermined portion of a first reagent for substantially lysing the red blood cells in the whole blood sample, wherein the first reagent includes: a saponin compound; and an acid; and quenching the lysing action of said first reagent by the addition of a predetermined portion of a second reagent, wherein the second reagent includes a base and has a pH value of about 8 to about 12 to give a solution containing substantially lysed red blood cells, leukocytes and a pH value of about 3 to about 6. It is preferred in one illustrative embodiment that the saponin compound is selected from saponin; heat-treated saponin, saponin modified by heating in the presence of a halogenated carboxylic acid and combinations of these and similar such compounds. Another preferred and illustrative embodiment is formulated such that the acid is selected from halogenated carboxylic acids, phosphoric acid or combinations of these and similar such compounds. Further it should be noted that the reagent for lysing red blood cells may further be formulated to include a surfactant, preferably selected from non-ionic surfactants, cationic surfactants and combinations of these and similar such compounds. More preferably, the surfactant is selected from ethoxylated decylalcohols; ethoxylated and propoxylated linear (C8-C10) aliphatic alcohols and combinations of these and similar such compounds.

These and other features of the claimed subject matter are more fully set forth in the following description of preferred or illustrative embodiments.

BRIEF DESCRIPTION OF THE DRAWING

Features of the present invention as well as a preferred mode of use, further objectives, and advantages thereof, will best be understood by reference to the following detailed description of an illustrative embodiment when read in conjunction with the accompanying drawing, wherein.

DESCRIPTION OF ILLUSTRATIVE EMBODIMENTS

Red Blood Cell Lyse Agent

Figure 1:
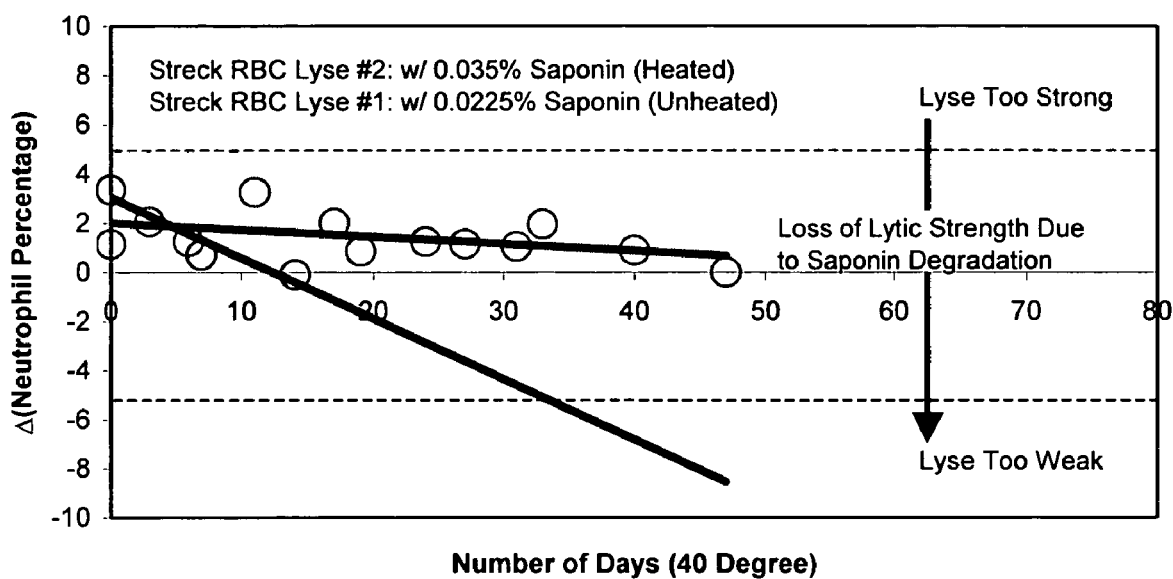
FIG. 1 illustrates comparison of lytic stability of the red blood cell lyse solutions at 40° C. in accordance with the present invention.

The red blood cell lyse agent of the claimed subject matter preferably includes first component for lysing red blood cell components of a blood sample, a second component that is an acid, and an optional third component that functions as a surfactant. The combination of reagents is designed to achieve a final acidic medium, ranging from about pH 3 to about 6, preferably from about 4 to about 5, is used to stabilize the white blood cells and continuously remove red blood cell fragments.

An example of a suitable first component is preferably saponin, although other art disclosed agents including modified saponin or saponin derivatives or other saponin like compounds may also be employed. As the term is used herein, the term "a saponin compound" or just "saponin" is defined as including such modified saponin or saponin derivatives that retain the functionality of saponin as well as saponin itself. Modified saponin derivatives are synthesized by heating at 121° C. in solution containing chloroacetic acid and surfactant. Such saponin derivatives are significantly different from the original saponin. The modification allows (1) a much broader range of saponin derivative concentration, ranging from 0.020%-0.035%, which can be used in the red blood cell lyse; and (2) a significantly longer stability for the reagents.

The acid of the second component may be any suitable acid. For example, it may be phosphoric acid, sulfuric acid, hydrochloric acid or other acid of like characteristics for the present intended environment. The acid may be an organic acid, an inorganic acid or a combination thereof. In one embodiment, it is a halogenated organic acid. More preferably it is a halogenated carboxylic acid, such as monochloroacetic acid. A preferred acid is one that is substantially free of formic acid, acetic acid or respective mixtures thereof. In one embodiment, it is contemplated that the third component is omitted altogether, with saponin or saponin derivative acting instead also as a surfactant.

The surfactant may be one or more of a non-ionic, cationic, anionic, or amphoteric surfactant. In a highly preferred embodiment it is a non-ionic surfactant or a cationic surfactant. In one embodiment, it is preferable to employ a surfactant that is substantially free of polyoxyethylene groups. For example, one preferred class of surfactants includes halogen-capped (e.g., chlorine capped) surfactants, linear alcohol based surfactants, alkoxylated (e.g., ethoxylated or propoxylated) alcohol surfactants. Examples of suitable commercially available surfactants include, without limitation, Rhodasurf DA630, Rhodasurf 10060, Rhodasurf 8 D 75, Antarox BL 240 or the like. Preferably the surfactant is generally stable in either an acid or an alkali medium. Rhodasurf DA 630 and other possible choices of surfactants are used to effectively remove the RBC fragments during the procedure of lysis.

The amounts of the respective components are sufficient for yielding a red blood cell lyse agent that is hypotonic. More preferably, the resulting lyse agent will have an osmolality of less than about 50 mOsm, and more preferably less than about 35 mOsm. For example, a preferred range is about 10 to about 30 mOsm. The pH of the red blood cell lyse agent preferably is about 2 to about 4, and more preferably about 2.2 to about 3.2.

Thus, one preferred composition employs an acid in an amount of about 0.001% weight per volume to about 1% weight per volume, and more preferably about 0.05 to about 0.5% weight per volume. Saponin or saponin derivative is employed in an amount of about 0.005 to about 0.1% weight per volume, and more preferably about 0.01 to about 0.04% weight per volume. Any surfactant employed is present in an amount of about 0.005 to about 0.07% weight per volume, and more preferably about 0.01 to about 0.05% weight per volume.

The red blood cell lyse is preferably contacted with a blood sample prior to analysis by an automated instrument of one or more white blood cell populations (e.g., by light scatter, impedance or other art-disclosed techniques). The sample is contacted for a sufficient time so that red blood cells are lysed and will not interfere with white blood cell analysis.

Quench

It is seen from the above that promptly after contacting the blood sample with the red blood cell lyse, it is desirable to quench a substantial portion of the remaining white blood cell fraction of the blood. This is accomplished by raising the osmolality to isotonicity and bringing the pH to a value of approximately 4.5. The quench is used to achieve a final acidic medium, ranging from about pH 3 to about 6, preferably from about 4 to about 5, which is designed to stabilize the white blood cells and continuously remove red blood cell fragments.

A preferred quench composition will include a first component, which is generally basic, and at least one other component that includes a salt (or another buffer material, such as those disclosed elsewhere herein). For example, one preferred embodiment contemplates the use of a metal sulfate, such as an alkali metal sulfate (e.g., sodium sulfate) in an amount of about 0.5 to about 10% weight, more preferably about 1 to about 7% weight, and still more preferably about 2 to about 4% weight. An alkali metal salt, halide salt, or a mixture thereof, is also preferred as comprising the salt component, such as sodium chloride. The salt is present in an amount of about 0.1 to about 10% weight, more preferably about 0.5 to about 7% weight, and still more preferably about 1 to about 4% weight. A metal carbonate may also be employed, such as sodium carbonate, e.g., in an amount ranging from about 0.01 to about 1% weight.

The amounts of the respective components are sufficient for yielding a quench that is generally hypertonic, though its use following a red blood cell lyse will generally yield the blood sample subjected to a generally isotonic environment. More preferably, the resulting quench will have an osmolality of greater than about 750 mOsm. For example, a preferred range is about 900 to about 1100 mOsm. The pH of the quench preferably is about 8 to about 12, and more preferably about 9 to about 11.

The amount of the quench utilized should result in a final solution having a pH value of about 3.0 to about 6.0 and preferably from about 4 to about 5. That is to say a slightly acid solution is produced to stabilize the leukocytes and preserve the differentiation of leukocytes.

The quench is preferably filtered in a suitable manner, such as by using a filter membrane (e.g., a cellulose nitrate membrane, such as a Nalgene 0.2 CN filter) or the like.

Diluent

The claimed subject matter also contemplates the employment of a diluent, preferably after the sample has been quenched. The diluent thus functions as a sheath agent for carrying the sample through a flow cell of an instrument. A preferred diluent is generally isotonic and has a pH of between about 6.5 and 7. The diluent preferably is water or saline based composition and may include one or a combination of a buffer, a chelating agent, a stabilizer or an anti-microbial. Examples of suitable ingredients for the diluent include, without limitation, one or a combination of ammonium sulfate, boric acid, EDTA, EDTA disodium, glycine, potassium phosphate, sodium bicarbonate, sodium carbonate, sodium chloride, sodium citrate, sodium phosphate, tris hydrochloride, omadine, procaine or the like.

The red blood cell lyse agent of the claimed subject matter is contacted with red blood cells of a blood sample for lysing the same. The quench is thereafter (e.g., within about 30, and more preferably about 5-10 seconds of red blood cell lysing) contacted with the blood sample. Following the quench, the white blood cells of the sample are analyzed by an instrument (e.g., an instrument for differentiating the subpopulations of white blood cells, a flow cytometer, or other like instrument).

One illustrative composition includes a combination of two or more of the following ingredients in a water base:

Sodium sulfate about 0.1 to about 3% weight
Sodium chloride about 0.1 to about 1% weight
Sodium phosphate dibasic about 0.1 to about 3% weight
Sodium phosphate monobasic about 0.01 to about 0.2% weight
Preservative (e.g., EDTA disodium) about 0.001 to about 0.5% weight
Disinfectant (e.g. Sodium omadine) about 0.05 to about 1 mL/L.
Procaine about 0.001% to about 1% weight Various other possible art-disclosed ingredients may be employed in the reagents herein including for example those disclosed in U.S. Pat. Nos. 5,731,206; 5,928,949; 4,751,179; 5,155,044; 5,786,224; 5,817,518; 5,686,308, or the like, all of which are hereby incorporated by reference.

It will be appreciated that the claimed subject matter also can be employed in the analysis of blood controls, such as those found in one or more of U.S. Pat. Nos. 6,200,500; 6,221,668; 5,731,205; 5,529,933; 6,362,003; 5,994,139; 5,858,790; 6,444,471, or the like, all of which are hereby incorporated by reference. The claimed subject matter thus also contemplates the packaging of the reagents of the claimed subject matter along with the controls disclosed in the above patents or as part of a kit as disclosed in the above patents. The claimed subject matter additionally or alternatively may be packaged as part of a kit in combination with other reagents, such as a lysing agent (e.g., a cyanide-free lysing agent). The compositions of the claimed subject matter can also be employed as part of a calibration procedure for an automated instrument.

In another preferred embodiment of the claimed subject matter the red blood cell lyse, the quench, another reagent or a combination thereof can further include a lipoprotein, and more preferably a high density lipoprotein (e.g., SUPERTRATE™, from Bayer) that is brought into contact with the white blood cells of the blood sample.

In the use of the claimed subject matter, it is contemplated in one aspect that a blood sample is provided to a laboratory in a suitable container, and preferably one that includes an anti-coagulant and optionally one or more agents for preserving surface antigens on the surfaces of blood cells in the sample. An example of one suitable system for such application is disclosed in commonly owned U.S. patent application Ser. No. 60/418,978, filed Oct. 16, 2002, hereby incorporated by reference (entitled: "METHOD AND DEVICE FOR COLLECTING AND PRESERVING CELLS FOR ANALYSIS").

In accordance with one highly preferred aspect of that technology, there is contemplated a method of making a collection device for cells comprising: providing a tube having an open end and a closed end; preloading compounds including: i) an anticoagulant agent, and ii) a fixative agent consisting of diazolidinyl urea into said tube, wherein said compounds are in a sufficient amount to preserve said cells' original morphology and antigenic sites without significant dilution of said cells, and thereby allowing said cells to be directly analyzed by an instrument such as a flow cytometer without further treatment; inserting a closure into said open end of said tube; and drawing a vacuum inside said tube to a predetermined level to form said collection device.

It will be appreciated from the above that use of the reagents of the claimed subject matter may be done in an environment that is substantially free of one or more of the following: 1) dye (e.g., a fluorochrome dye) 2) a combination of saponin or saponin derivative and a nonhalogenated carboxylic acid; 3) an acid selected from formic acid, acetic acid and mixtures thereof; 4) a combination of saponin or saponin derivative and sulphonic acid; 5) a cross-linking agent such as an aldehyde; 6) an alkali metal salt of an alkyl sulfate anionic surfactant (e.g., as defined in U.S. Pat. No. 5,786,224); 7) an ethoxylated long chain amine (e.g., as defined in U.S. Pat. No. 5,686,308); or 8) combinations of these compounds The following examples are included as demonstrative preferred embodiments. It should be appreciated by those of skill in the art that the techniques disclosed in the examples which follow represent techniques discovered by the inventors to function well in the practice of what is claimed, and thus can be considered to constitute preferred modes of practice. However, those of skill in the art should, in light of the present disclosure, appreciate that many changes can be made in the specific embodiments which are disclosed and still obtain a like or similar result without departing from the scope of what is claimed.

The following Examples 1-3, when employing an isotonic diluent, employ the diluent substantially described in Example 4.

EXAMPLE 1

An illustrative red blood cell lyse solution was formulated as follows:

| | |
|---|---|
| Chloroacetic acid | 0.1% weight |
| Saponin | 0.0225% weight |
| Rhodasurf DA 630 | 0.025% weight/volume |
| Water or isotonic diluent | balance |

The composition exhibits a pH of about 2.5 and an osmolality of about 15 mOsm.

It should be noted that Rhodasurf (formerly Emulphogene) DA 630: is an ethoxylated decylalcohol, CAS 26183-52-8; non-ionic; liquid 100% conc.; HLB=12.5; cloud point=42° C. (1% aq.); acid and alkali stable. It is described as being a low-foaming rapid wetting agent; dispersant for industrial, institutional and household cleaners, textile scouring; intermediate for manufacturing of esters for textile and industrial applications; emulsifier for deformers. Similar products include Rhodasurf ID 060 (HLB=12) and Rhodasurf 8 D 75 (HLB=14).

EXAMPLE 2

An illustrative red blood cell lyse solution was formulated as follows:

| | |
|---|---|
| Chloroacetic acid | 0.1% weight |
| Saponin | 0.0225% weight |
| Antarox BL 240 | 0.025% weight/volume |
| Water or isotonic diluent | balance |

The composition exhibits a pH of about 2.5 and an osmolality of about 15 mOsm.

It should be noted that Antarox BL 240: is described as an ethoxylated and propoxylated linear (C8-C10) aliphatic alcohols, CAS 68603-25-8; non-ionic; liquid 100% act.; bland odor; water sol.; sp. gr.=0.99; visc.=35 cps; surf tension=28 dyns/cm (0.1%); cloud point=38-42° C. (1% aq.); flash point=124° C.; pour point <21° C. biodegradable, most water-soluble member of BL-200 series. Recognized uses include low-foaming detergent; wetting agent for metal cleaning, (high-temperature) rinse aids, textiles, floor cleaners.

EXAMPLE 3

An illustrative quench solution was formulated as follows:

| | |
|---|---|
| Sodium sulfate | 3.13% weight |
| Sodium chloride | 1.85% weight |
| Sodium carbonate | 0.15% weight |
| Water or isotonic diluent | balance |

The composition is filtered by a Nalgene 0.2 CN filter. The composition exhibits a pH of about 10.5 and an osmolality of about 1050 mOsm.

EXAMPLE 4

An illustrative isotonic diluent solution was formulated as follows:

| | |
|---|---|
| Sodium sulfate | 0.822% weight |
| Sodium chloride | 0.484% weight |
| Sodium phosphate dibasic | 0.103% weight |
| Sodium phosphate monobasic | 0.059% weight |
| EDTA disodium | 0.010% weight |
| Sodium omadine | 0.25 mL/L |
| Procaine | 0.0122% weight |

The composition is filtered a 0.45 µm capsule filter. The composition exhibits a pH of about 6.9 and an osmolality of about 315 mOsm.

The above reagents can be used in a STK-S, a GEN-S, a MAXM, and a LH 750 analyzer all commercially available and/or sold by BeckmanCoulter and yields reliable and reproducible blood analysis data. The reagents of Examples 1 and 2 are contacted with red blood cells of a blood sample for lysing the same. The reagent of Example 3 is thereafter (e.g., within about 30, and more preferably about 5-10 seconds of red blood cell lysing) contacted with the blood sample. Following the quench, the instrument analyzes the white blood cells of the sample by passing the cells through a flow cell of the instrument (e.g., an instrument for differentiating the subpopulations of white blood cells, a flow cytometer, or other like instrument) carried in a suitable diluent, such as that of Example 4. Successful results can also be achieved when the chloroacetic acid of Examples 1 and 2 is substituted with a phosphoric acid in an amount of about 0.05% weight.

EXAMPLE 5

Modified Saponin can be used in the formulation of the lyse solutions substantially described above. An early study showed that the red blood cell lyse using original (0.0225%, un-heated) saponin failed to perform on Beckman Coulter hematology analyzers after 8 months at room temperature. Another study showed that the red blood cell lyse lost approximately 45% of the saponin activity after 8 months.

The purpose of this study is to explore the possibility to improve the saponin stability by a heating procedure. It is known that such intensive heating procedure reduces the saponin activity, possibly by removing the unstable lytic components from saponin. The remaining lytic components in saponin may have a longer stability in solution.

Stock solution (heated) contained:

| | |
|---|---|
| Chloroacetic acid: | 0.1% weight |
| Saponin | 5.000% weight |
| DA-630 | 0.025% weight |

Base solution (not heated) contained:

| | |
|---|---|
| Chloroacetic acid: | 0.1% weight |
| Saponin | 5.000% weight |
| DA-630 | 0.025% weight |

The stock solution is autoclaved (Cycle 1, 121° C. for 30 minutes) and double filtered using Nalgene 0.8 µm and 0.2 µm filters. The red blood cell lyse is prepared by mixing the stock solution and the base solution at a calculated ratio to achieve the desired final formulation.

Modified Saponin Derivatives: The procedure of heating results in a derivative of saponin. The product, as well as the original saponin, were analyzed by HPLC.

A review of the results indicates that the most distinctive change due to the modification was the generation of an additional peak (eluted at 10 minute). Further study showed that the additional peak did not have any lytic capability, while the first three peaks retained the lytic function. This result suggests that the heating procedure removed some unstable components of saponin. Without the heating procedure, such unstable components may degrade slowly at room temperature.

It has been found that a broader range of saponin derivative can be applied to the red blood cell lyse solution formulation.

When the red blood cell lyse solution is outside of a very narrow concentration range of saponin (i.e. 0.0200%-0.0225%), the red blood cell lyse does not perform properly. This problem was especially true if too much or too little saponin was used in the formulation. For example the following table is illustrative of the data gathered.

|        | Concentration of Saponin |         |         |         |
|--------|---------|---------|---------|---------|
|        | 0.0175% | 0.0200% | 0.0225% | 0.0250% |
| STK-S  | Bad     | Good    | Good    | Bad     |
| GEN•S  | Bad     | Marginal| Good    | Marginal|

The modification of saponin by heating at 121° C. has been found to allow a much broader concentration range (i.e. 0.0200%-0.0350%) of the saponin derivative in the red blood cell lyse solution. Such a broad range for the concentration of the saponin component brings a high flexibility to the red blood cell lyse, and subsequently, a much longer stability. Data illustrative of this result is provided in the following table:

|        | Concentration of Saponin | | | | | |
|--------|--------|--------|--------|--------|--------|--------|
|        | 0.020% | 0.025% | 0.030% | 0.035% | 0.040% | 0.050% |
| STK-S  | Good   | N/A    | N/A    | Good   | N/A    | N/A    |
| GEN•S  | Good   | Good   | Good   | Good   | Marginal | Bad  |

The relative lytic strength of the red blood cell solution substantially disclosed herein was compared to the prior art reagents commercially available from Coulter. FIG. 1, provides an illustrative comparison of the 40-degree C. stability of the red blood cell lyse solutions. The value of $\Delta NE$ (% NE using the reagents disclosed herein—% NE using prior art reagents available from Coulter) for STaK Chex Low was used to evaluate the possible loss of lytic strength.

Upon review of this data one of skill in the art should appreciate that no apparent loss of lytic strength was revealed for the autoclaved saponin derivatives for 47 days at 40° C. In contrast a measurable amount of loss of lytic strength was observed for the un-autoclaved saponin.

In view of the above disclosure, one of ordinary skill in the art should understand and appreciate that one illustrative embodiment of the claimed subject matter includes a reagent system for substantially lysing red blood cells in a whole blood sample prior to leukocyte analysis. In one such illustrative embodiment, the reagent system includes a first reagent for substantially lysing the red blood cells in the whole blood sample, and a second reagent for quenching the activity of the first reagent, wherein the second reagent includes a base and has a pH value of about 8 to 12. A final acidic medium, ranging from about pH 3 to about 6, preferably from about 4 to about 5, is used to stabilize the white blood cells and continuously remove red blood cell fragments. The first reagent is formulated to include: a saponin compound; an acid, preferably selected from halogenated carboxylic acids, phosphoric acid or combinations of these and similar compounds that should be known to one of skill in the art. Optionally the first reagent may further include a surfactant preferably selected from non-ionic surfactants, cationic surfactants and combinations of these and similar compounds that should be known to one of skill in the art. In one specific and illustrative embodiment, the surfactant is selected from ethoxylated decylalcohols, ethoxylated and propoxylated linear (C8-C10) aliphatic alcohols, and combinations of these and similar compounds that should be known to one of skill in the art. It should be appreciated that the saponin compound is preferably selected from the group including saponin; heat-treated saponin, saponin modified by heating in the presence of a halogenated carboxylic acid and combinations of these and similar compounds that should be known to one of skill in the art.

Another illustrative embodiment of the claimed subject matter includes A reagent system formulated to include: a reagent for lysing red blood cells; and a quench; such that the system is substantially free of compounds including: i. dye; ii. a combination of saponin and carboxylic acid; iii. an acid selected from formic acid, acetic acid and mixtures thereof; iv. a combination of saponin and sulphonic acid; v. a cross-linking agent such as an aldehyde; vi. an alkali metal salt of an alkyl sulfate anionic surfactant; vii. an ethoxylated long chain amine; and combinations thereof. Preferably the illustrative reagent for lysing red blood cells includes a saponin compound and an acid. The saponin compound can be selected from saponin; heat-treated saponin, saponin modified by heating in the presence of a halogenated carboxylic acid and combinations of these and similar compounds that should be known to one of skill in the art. The acid portion of the reagent system is selected from halogenated carboxylic acids, phosphoric acid or combinations of these and similar compounds that should be known to one of skill in the art. The reagent for lysing red blood cells may further includes a surfactant. The surfactant can be selected from non-ionic surfactants, cationic surfactants and combinations thereof and preferably the surfactant is selected from ethoxylated decylalcohols, ethoxylated and propoxylated linear (C8-C10) aliphatic alcohols, and combinations of these and similar such compounds.

It will also be appreciated by one or ordinary skill in the art that a present illustrative embodiment of the claimed subject matter includes a method of lysing the red blood cells and stabilizing white blood cells present in a sample of whole blood. In one such illustrative embodiment, the method includes: combining a predetermined portion of the sample of whole blood with a predetermined portion of a first reagent for substantially lysing the red blood cells in the whole blood sample, wherein the first reagent includes: a saponin compound; and an acid; and quenching the lysing action of said first reagent by the addition of a predetermined portion of a second reagent, wherein the second reagent includes a base and has a pH value of about 8 to about 12 to give a solution containing substantially lysed red blood cells, leukocytes and a pH value of about 3 to about 6. It is preferred in one illustrative embodiment that the saponin compound is selected from saponin; heat-treated saponin, saponin modified by heating in the presence of a halogenated carboxylic acid and combinations of these and similar such compounds. Another preferred and illustrative embodiment is formulated such that the acid is selected from halogenated carboxylic acids, phosphoric acid or combinations of these and similar such compounds. Further it should be noted that the reagent for lysing red blood cells may further be formulated to include a surfactant, preferably selected from non-ionic surfactants, cationic surfactants and combinations of these and similar such compounds. More preferably, the surfactant is selected from ethoxylated decylalcohols, ethoxylated and propoxylated linear (C8-C10) aliphatic alcohols, and combinations of these and similar such compounds.

While the apparatus, compositions and methods disclosed above have been described in terms of preferred or illustrative embodiments, it will be apparent to those of skill in the art that variations may be applied to the process described herein without departing from the concept and scope of the claimed subject matter. All such similar substitutes and modifications apparent to those skilled in the art are deemed to be within the scope and concept of the subject matter as it is set out in the following claims.

What is claimed is:

1. A reagent system for substantially lysing red blood cells in a whole blood sample prior to leukocyte analysis, the reagent system comprising:
    (a) a first reagent for substantially lysing the red blood cells in the whole blood sample, wherein the first reagent includes a saponin compound, an acid selected from the group consisting of a halogenated carboxylic acid, a phosphoric acid and a combination thereof, and an additional surfactant selected from the group consisting of a non-ionic surfactant, a cationic surfactant and a combination thereof, wherein the first reagent is autoclaved at about 121° C.; and
    (b) a second reagent for quenching the activity of the first reagent, wherein the second reagent includes a base and has a pH value of about 8 to 12.

2. The reagent system of claim 1, wherein the non-ionic surfactant is selected from the group consisting of ethoxylated decylalcohols, an ethoxylated and propoxylated linear (C8-C10) aliphatic alcohols, and a combination thereof.

3. A method of lysing red blood cells and stabilizing white blood cells present in a whole blood sample, the method comprising the steps of:
    (a) combining a predetermined portion of the whole blood sample with a predetermined portion of a first reagent to substantially lysing the red blood cells in the whole blood sample, wherein the first reagent includes a saponin compound, an acid and an additional surfactant selected from the group consisting of a non-ionic surfactant, a cationic surfactant and a combination thereof, wherein the first reagent is autoclaved at about 121° C.; and
    (b) quenching the lysing action of said first reagent by the addition of a predetermined portion of a second reagent to result in a solution containing leukocytes and substantially lysed red blood cells and having a pH value of about 3 to about 6, wherein the second reagent includes a base and has a pH value of about 8 to about 12.

4. The method of claim 3, wherein the acid is selected from the group consisting of halogenated carboxylic acids, a phosphoric acid and a combinations thereof.

5. The method of claim 3, wherein the non-ionic surfactant is selected from the group consisting of an ethoxylated decylalcohols, an ethoxylated and propoxylated linear (C8-C10) aliphatic alcohols, and combinations thereof.

6. A method of preparing a whole blood sample for leukacyte analysis, comprising the steps of:
    (a) substantially lysing red blood cells in at least a portion of the whole blood sample by adding a saponin compound, an acid and an additional surfactant selected from the group consisting of a non-ionic surfactant, a cationic surfactant and a combination thereof, to the sample to form a mixture, wherein said saponin compound, acid and additional surfactant are autoclaved together at about 121° C.; and
    (b) substantially quenching the mixture by bringing the pH value of the mixture to about 3 to about 6.

7. The method of claim 6, wherein the pH value of the mixture is from about 4 to about 5.

* * * * *

UNITED STATES PATENT AND TRADEMARK OFFICE
CERTIFICATE OF CORRECTION

PATENT NO. : 7,247,484 B2  Page 1 of 1
APPLICATION NO. : 10/699502
DATED : July 24, 2007
INVENTOR(S) : Jiong Wu and Wayne L. Ryan It is certified that error appears in the above-identified patent and that said Letters Patent is hereby corrected as shown below:

Column 11, line 18, after the word "of" insert -- an --.

Column 11, line 19, delete "decylalcohols" and insert -- decylacohol --.

Column 11, line 20, delete "alcohols" and insert -- alcohol --.

Column 11, line 26, delete "lysing" and insert -- lyse --.

Column 12, line 9, after the word "of" insert -- a --.

Column 12, line 9, delete "acids" and insert -- acid --.

Column 12, line 10, delete "combinations" and insert -- combination --.

Column 12, line 13, delete "decylalcohols" and insert -- decylalcohol --.

Column 12, line 14, delete "alcohols" and insert -- alcohol --.

Column 12, line 14, after the word "and" insert -- a --.

Column 12, line 14, delete "combinations" and insert -- combination --.

Column 12, line 16, delete "leukacyte" and insert -- leukocyte --.

Column 12, line 21, delete the comma after the word "thereof".

Signed and Sealed this

Second Day of October, 2007

JON W. DUDAS
*Director of the United States Patent and Trademark Office*